US006015785A

United States Patent [19]
Shen et al.

[11] Patent Number: 6,015,785
[45] Date of Patent: *Jan. 18, 2000

[54] AGLUCONE ISOFAVONE ENRICHED VEGETABLE PROTEIN EXTRACT AND ISOLATE AND PROCESS FOR PRODUCING

[75] Inventors: Jerome L. Shen, St. Louis; Barbara A. Bryan, University City, both of Mo.

[73] Assignee: Protein Technologies International, Inc., St. Louis, Mo.

[*] Notice: This patent is subject to a terminal disclaimer.

[21] Appl. No.: 08/961,829

[22] Filed: Oct. 31, 1997

Related U.S. Application Data

[63] Continuation of application No. 08/307,752, Apr. 12, 1996, Pat. No. 5,763,389.
[51] Int. Cl.[7] .......................... A61K 31/35; A61K 38/02; C07K 14/415; C12P 17/06
[52] U.S. Cl. .............................. 514/2; 514/455; 514/456; 530/370; 530/378
[58] Field of Search .................................. 435/68.1, 125; 514/2.8, 455, 456; 530/343, 370, 377, 378, 407, 412, 414, 419, 420, 427; 549/403

[56] References Cited

U.S. PATENT DOCUMENTS

| | | | |
|---|---|---|---|
| 3,870,805 | 3/1975 | Hayes et al. | 426/148 |
| 3,949,085 | 4/1976 | Feuer et al. | 514/455 |
| 4,064,277 | 12/1977 | Yokotsuka et al. | 426/331 |
| 4,157,984 | 6/1979 | Zilliken | 252/407 |
| 4,163,746 | 8/1979 | Feuer et al. | 549/403 |
| 4,218,489 | 8/1980 | Zilliken | 426/545 |
| 4,232,122 | 11/1980 | Zilliken | 435/52 |
| 4,259,358 | 3/1981 | Duthie | 426/46 |
| 4,264,509 | 4/1981 | Zilliken | 426/545 |
| 4,366,082 | 12/1982 | Zilliken | 252/404 |
| 4,366,248 | 12/1982 | Zilliken | 435/125 |
| 4,390,559 | 6/1983 | Zilliken | 426/545 |
| 4,424,151 | 1/1984 | Grealy et al. | 426/656 |
| 5,320,949 | 6/1994 | Shen | 435/68.1 |
| 5,352,384 | 10/1994 | Shen | 252/398 |
| 5,424,331 | 6/1995 | Shlyankevich | 514/456 |
| 5,506,211 | 4/1996 | BNarnes et al. | 514/27 |
| 5,516,528 | 5/1996 | Hughes et al. | 424/464 |
| 5,569,459 | 10/1996 | Shlyankevich | 424/195.1 |
| 5,637,561 | 6/1997 | Shen et al. | 514/2 |
| 5,637,562 | 6/1997 | Shen et al. | 514/2 |
| 5,763,389 | 6/1998 | Shen et al. | 514/2 |

FOREIGN PATENT DOCUMENTS

| | | |
|---|---|---|
| 647408 | 4/1995 | European Pat. Off. . |
| 61-247396 | 11/1986 | Japan . |
| 1-258669 | 10/1989 | Japan . |
| 258669 | 10/1989 | Japan . |
| 5-170756 | 7/1993 | Japan . |
| 8-214787 | 8/1996 | Japan . |
| 8-283283 | 10/1996 | Japan . |
| 9-023822 | 1/1997 | Japan . |
| 93/23069 | 11/1993 | WIPO . |
| 95/10512 | 4/1995 | WIPO . |
| 95/10529 | 4/1995 | WIPO . |
| 95/10530 | 4/1995 | WIPO . |
| 95/16362 | 6/1995 | WIPO . |
| 96/10341 | 4/1996 | WIPO . |
| 97/07811 | 3/1997 | WIPO . |

OTHER PUBLICATIONS

Matsuura et al, Beta–Glucosides from soybeans hydrolyze daidzin and genistin. J. Food Science, vol. 58, No. 1, pp. 144–147, 1993.

Eldridge, Determination of isoflavones in soybean flours, protein concentrates, and isolates. J. Agric. Food Chem., vol. 30, pp. 353–355, 1982.

Matsurra et al, Objectionable Flavor of Soy Milk Developed during the Soaking of Soybeans and its Control. J. Food Science, vol. 54, No. 3, pp. 602–605, 1989.

Wang et al, Isoflavone Content in Commercial Soybean Foods. J. Agric. Food Chem., vol. 42, No. 8, pp. 1666–1673, 1994.

Wang et al, Isoflavone Composition of American and Japanese Soybeans in Iowa: Effects of Variety, Crop Year, and Location. J. Agric. Food Chem., vol. 42, pp. 1674–1677, 1994.

Soybeans: Chemistry and Technology, pp. 187–188, 1978.

Soybean Utilization, Chapter 2—Morphology and Composition, pp. 64–66, 1987.

Anyanwutaku et al, Isoflavonoids from Streptomycetes: Origins of Genistein, 8–Chlorogenistein, and 6,8–Dichlorogenistein. J. Natural Products, vol. 55, No. 10, pp. 1498–1504, 1992.

Gooderlam et al, A Soy Protein Isolate Rich in Genestein . . . J. Nutrition, vol. 126/8, pp. 2000–2006. Abstract only, 1996.

Bohm et al, Health Relevance of Soya Beans due to their Isoflavonoid Content. Z. Lebensmittelwirtsch, vol. 47, No. 12, pp. 55–57. Abstract only, 1996.

(List continued on next page.)

*Primary Examiner*—Jeffrey E. Russel
*Attorney, Agent, or Firm*—Richard B. Taylor

[57] ABSTRACT

Aglucone isoflavone enriched vegetable protein extract and isolate and process for producing and recovering are disclosed. The aglucone isoflavone extract is made by extracting a vegetable protein material comprising glucone isoflavones with an aqueous extractant having a pH above about the isoelectric point of the protein material to produce an aqueous extract, and reacting the glucone isoflavones with a sufficient amount of beta-glucosidase enzyme or esterase enzyme for a time period, temperature, and pH sufficient to convert at least a majority of the glucone isoflavones in the extract to aglucone isoflavones and thereby produce the aglucone isoflavone enriched extract. The aglucone isoflavone enriched isolates are produced by adjusting the pH of the reacted extract to about the isoelectric point of the vegetable protein material to precipitate the protein material, and separating the protein material to produce an aglucone enriched protein isolate.

2 Claims, No Drawings

OTHER PUBLICATIONS

Kuhn, Soy in the Spotlight. Food Process, vol. 57, No. 5, pp. 52–58. Abstract only, 1996.

Setchell et al, Mammalian Lignans and Phyto–estrogens . . . Role of the Gut Flora in Toxicity and Cancer, Chapter 14, pp. 315–345, 1988.

Franke et al, Quantitation of Phytoestrogens in Legumes by HPLC. J. Agric. Food Chem., vol. 42, pp. 1905–1913, 1994.

Knight et al, A Review of Phytoestrogens and Their Effects in Relation to Menopausal Symptoms. Australian J. of Nut. and Dietetics, 53:1, pp. 5–11, 1996.

Murphy et al, Total Genestein and Daidzein Content of Soyfoods. Food Compositions, Abstract 4283, No date.

Nguyenle et al, An Investigation on the extraction and concentration of isoflavones in soy–based products. J. Pharm. Biomed. Analysis, vol. 14, pp. 221–232, 1995.

Isoflavones and Their conjugates in Soy Foods . . . Food Chem., vol. 42, pp. 2466–2474, 1982.

AGLUCONE ISOFAVONE ENRICHED VEGETABLE PROTEIN EXTRACT AND ISOLATE AND PROCESS FOR PRODUCING

This application is a continuation application of U.S. application Ser. No. 08/307,752 filed on Apr. 12, 1996 now U.S. Pat. No. 5,763,389.

FIELD OF THE INVENTION

The present invention relates to the production of an extract and isolate enriched with aglucone isoflavones, by extraction of soluble material from a vegetable protein material and treatment with one or more beta-glucosidase enzymes under conditions such that a majority of the glucone isoflavones are converted to aglucone isoflavones which are retained in the protein isolate.

BACKGROUND OF THE INVENTION

Isoflavones occur in a variety of leguminous plants, including vegetable protein materials such as soybeans. These compounds include daidzin, 6"-OAc daidzin, 6"-OMal daidzin, daidzein, genistin, 6"-OAc genistin, 6"-OMal genistin, genistein, glycitin, 6"-OMal glycitin, glycitein, biochanin A, formononetin, and coumesterol. Typically these compounds are associated with the inherent, bitter flavor of soybeans, and in the production of commercial products, such as isolates and concentrates, the focus has been to remove these materials. For example, in a conventional process for the production of a soy protein isolate in which soy flakes are extracted with an aqueous alkaline medium, much of the isoflavones are solubilized in the extract, and remain solubilized in the whey, which is usually discarded following acid precipitation of the protein to form an isolate. Residual isoflavones left in the acid precipitated protein isolate are usually removed by exhaustive washing of the isolate.

It has been recently recognized that the isoflavones contained in vegetable proteins such as soybeans may inhibit the growth of human cancer cells, such as breast cancer cells and prostate cancer cells as described in the following articles: "Genistein Inhibition of the Growth of Human Breast Cancer Cells, Independence from Estrogen Receptors and the Multi-Drug Resistance Gene" by Peterson and Barnes, *Biochemical and Biophysical Research. Communications*, Vol. 179, No. 1, pp. 661–667, Aug. 30, 1991; "Genistein and Biochanin A Inhibit the Growth of Human Prostate Cancer Cells but Not Epidermal Growth Factor Receptor Tyrosine Autophosphorylation" by Peterson and Barnes, *The Prostate*, Vol. 22, pp. 335–345 (1993); and "Soybeans Inhibit Mammary Tumors in Models of Breast Cancer" by Barnes, et al., *Mutagens and Carcinogens in the Diet*, pp. 239–253 (1990).

Of the above isoflavones, several exist as glucosides, or as glucones, with a glucose molecule attached. Several of the glucones such as the 6"-OAc genistin, contain an acetate group attached to the six position of the glucose molecule itself. While all the isoflavones, including the glucosides are of interest in medical evaluation, the specific isoflavones of most interest are the aglucones, wherein the glucose molecule is not attached. These isoflavones are not as water soluble as the glucones or isoflavone glucosides. Specific isoflavones in this category are daidzein, genistein, and glycitein. These aglucones have the following general formula:

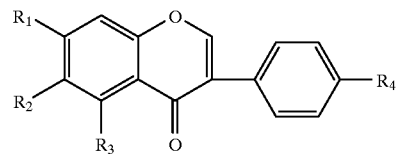

wherein, $R_1$, $R_2$, $R_3$ and $R_4$ may be selected from the group consisting of H, OH and $OCH_3$. It is therefore to the aglucones and enrichment of a vegetable protein isolate with these materials to which the present invention is directed.

Methods are known in the art for converting glucone isoflavones to aglucone isoflavones, such as described in Japanese Patent Application 258,669 to Obata et al. Such processes achieve only a moderate extent of conversion and so are not desirable, particularly for large scale commercial operations. In addition, known processes such as described in the '669 application teach removing the isoflavones from the protein material and do not describe how to prepare an aglucone isoflavone enriched protein extract or isolate. Thus, there is a need for a process of converting at least a majority and preferably substantially all glucone isoflavones to aglucone isoflavones, and for producing an aglucone isoflavone enriched protein extract and isolate.

It is therefore an object of the present invention to provide an aglucone isoflavone enriched extract and protein isolate, and a process for producing the same. This, and other objects, are specifically achieved in the detailed description of the present invention set forth below.

SUMMARY OF THE INVENTION

The present invention provides an aglucone isoflavone enriched vegetable protein extract and isolate and processes for producing such. The methods for producing such extracts comprise extracting a vegetable protein material comprising glucone isoflavones with an aqueous extractant having a pH above about the isoelectric point of the vegetable protein material, and reacting the glucone isoflavones with a sufficient amount of one or more beta-glucosidase enzymes for a time period, temperature, and pH sufficient to convert at least a majority of the glucone isoflavones in the extract to aglucone isoflavones, and thereby produce the aglucone isoflavone enriched extract. The present invention also provides methods for producing such extracts wherein supplemental beta-glucosidase is added to the extract to produce aglucone isoflavone enriched extract. The present invention further provides methods of obtaining an aglucone enriched protein isolate by adjusting the pH of the previously described extract to about the isoelectric point of the protein material to precipitate the protein material and produce a protein isolate which is enriched with aglucone isoflavones. The resulting aglucone isoflavone enriched isolate can then be separated and dewatered to form a dried enriched isolate. The present invention, in addition, provides methods of recovering, in relatively high proportions, isoflavones from vegetable protein materials.

DESCRIPTION OF THE PREFERRED EMBODIMENTS

Although the present invention will be described with respect to soybean products and although the process is particularly suited for the production of aglucone isoflavone enriched extracts and isolates from soybean material, nevertheless the present process is generally applicable to the production of protein extracts and isolates from a variety of vegetable protein sources which contain isoflavones. An example of such a source is a vegetable protein material comprising soy or soybean materials. The term "soybean material" as used herein refers to soybeans or any soybean derivative.

The starting material in accordance with the preferred embodiment extract or isolate is soybean flakes, from which the oil has been removed by solvent extraction. The flakes are extracted with an aqueous extractant having a pH above about the isoelectric point of the protein material, preferably a pH of about 6.0 to about 10.0 and most preferably a pH of about 6.7 to about 9.7. Typical alkaline reagents may be employed, if desired to elevate the pH of the aqueous extractant, such as sodium hydroxide, potassium hydroxide, and calcium hydroxide. The desired isoflavone compounds are typically solubilized in the aqueous extract. It is also desirable, in order to maximize recovery of these compounds in the aqueous extract that the weight ratio of soybean flakes to extract is controlled to specific levels in order to solubilize as much of the inherent isoflavones in the protein material as possible.

Extraction of the proteins and isoflavones can be carried out in a variety of ways including countercurrent extraction of the flakes at a weight ratio of aqueous extractant to flakes of about 8:1 to about 16:1, in which the initial extract is used to extract the flakes and provide an aqueous extract of protein and isoflavones. Alternatively, a two step extraction process can be used in which the weight ratio of extractant to flakes in the initial step comprises about 10:1, and then a second extraction of the flakes with fresh extractant takes place at a weight ratio of extractant to flakes of about 6:1, or less, so that the combined weight ratio of extractant to flakes in both steps does not exceed a total weight ratio of extractant to flakes of about 16:1.

After removal of insoluble materials, the resulting aqueous protein extract comprising solubilized isoflavones is then reacted with one or more beta-glucosidase enzymes in order to convert a majority, and preferably substantially all, the isoflavones in glucone form, with a glucose molecule attached, to an aglucone isoflavone. The optimum pH range for the beta-glucosidase enzymes will vary depending on the specific beta-glucosidase enzyme used, but typically will vary between about 4 and about 8. The pH of the extract is typically adjusted to about the pH range at which the specific enzyme is most active prior to reaction with the enzyme. The pH is typically adjusted by the addition of an edible acid, such as acetic, sulfuric, phosphoric, hydrochloric, or any other suitable reagent.

The beta-glucosidase enzyme may be naturally present in the soybean material or present from microbial growth, referred to herein as "residual" enzyme, or may be added to the protein extract. Added enzyme is referred to herein as "supplemental enzyme". Generally, if the concentration of residual enzyme in the soybean material or extract is insufficient to convert a majority, and preferably substantially all, the isoflavones in glucone form to aglucone form, then supplemental enzyme should be added. The amount of enzyme sufficient to perform the conversion of isoflavones, varies upon a multitude of factors including the types of enzymes present, distribution of enzyme concentrations, pH of the system, and activities of enzymes present. Once sufficient concentrations of enzymes are present, either via residual enzymes, supplemental enzymes, or both, the protein extract with solubilized isoflavones is reacted with the beta-glucosidase enzymes for a time period, temperature, and pH sufficient to convert at least a majority and preferably substantially all the glucone isoflavones contained in the extract to the aglucone form.

Preferred supplemental beta-glucosidase enzymes include Biopectinase 100L and 300L, Biopectinase OK 70L, Lactase F, and Lactozyme. Lactase F is available from Amano International Enzyme Co., Inc., P.O. Box 1000, Troy, Va. 22974, which has an optimum pH range of about 4 to about 6, and Lactozyme is available from Novo Industries, Enzyme Division, Novo Alle, DK-2880 Bagsvaerd, Denmark, which has an optimum pH range of about 7. Biopectinase 100L, Biopectinase 300L, and Biopectinase OK 70L are available from Quest International, Sarasota, Fla. Supplemental enzymes are added in amounts sufficient to convert at least a majority and preferably substantially all the glucone isoflavones to aglucones. In instances where it is necessary to add supplemental enzymes, the amount of enzyme added is about 0.5% to about 5% by weight of the protein precipitate on a dry basis.

Another class of suitable enzymes is that of esterase enzymes. These enzymes are believed to be well suited to the preferred embodiment processes described herein as they convert the acetate and malonate conjugates to glucone isoflavones by removing the acetate and malonate groups from the isoflavone conjugates. In the most preferred embodiment, both types of enzymes, beta-glucosidase and esterase enzymes are utilized.

The processes of the preferred embodiment are preferably one-step processes and achieve very high degrees of conversion of isoflavones (from glucone form to aglucone form), in relatively short time periods, and with relative ease and economy. The term "one-step" reaction process as used herein refers to a reaction process in which certain process parameter values are generally maintained over the course of the reaction process. These process parameters include pH and temperature.

The very high degrees of conversion are such that at least a majority, and preferably substantially all, the isoflavones in glucone form present in the soybean material extract, are converted to aglucone form. The term "a majority" refers to extent of conversion of glucone isoflavones to aglucone isoflavones of at least about 50%. The term "substantially all" refers to extent of conversion of glucone isoflavones to aglucone isoflavones of at least about 80%, and most preferably at least about 90%.

Although not wishing to be bound to any particular theory, it is believed that the surprisingly and unexpectedly high degrees of conversion of the processes described herein result from a combination of process parameters utilized during the one-step reaction process. It is preferred that the pH of the reaction system be maintained, or approximately so, at a value of from about 4 to about 8, and most preferably at a value at which the enzyme(s) are most active prior to reaction with the isoflavone conjugate(s) during the one-step reaction process. It is preferred that the temperature of the reaction system be maintained, or approximately so, at a temperature of from about 40° C. to about 60° C., and most preferably at a temperature of about 60° C. during the one-step reaction process. Generally, the time periods necessary to achieve conversion of substantially all glucone isoflavones to aglucones via the one-step processes described herein are from about 2 hours to about 24 hours.

After reaction with one or more beta-glucosidase enzymes, the pH is adjusted to the isoelectric point for soy protein, generally between about 4.0 to about 5.0 and preferably between about 4.4 to about 4.6 by the addition of an acid. Adjustment of the pH to the isoelectric point precipitates the protein in the form of a curd, which is enriched with the less soluble aglucones. Following precipitation, the curd or precipitated protein is separated from the whey such as by centrifugation to form a protein isolate enriched with aglucone isoflavones.

In the preferred embodiment, washing of the precipitated protein material is either avoided entirely, or minimized in order to substantially reduce removal of the aglucone isoflavones from the protein precipitate to thereby provide an aglucone isoflavone enriched isolate even though the aglucones are less soluble in water than other isoflavones. Washing of the acid precipitated protein with water may therefore be avoided completely, or be limited to a single washing with water during which the weight ratio of water to precipitated protein material is between about 2:1 to about 6:1. This lack of washing of the acid precipitated curd provides an isolate enriched with the desired levels of isoflavones, even though more extensive washing could be carried out with a lesser recovery of isoflavones. The moderate amount of washing provides a protein isolate having a dry basis content of about 1.5 to about 3.5 mg/gram of genistein, and a daidzein content of about 1.0 to about 3.0 mg/gram.

The acid precipitated protein is then dewatered by a combination of centrifugation or concentration, and is dried in a conventional manner. The preferred embodiment is not intended to be limited by a particular means of dewatering, although it is preferred to use conventional drying techniques such as spray drying to form a dried isolate. The processes described herein provide isolates which have increased amounts of aglucone isoflavones.

The present invention also provides methods of recovering isoflavones, in very high proportions, from a vegetable protein material such as a soybean material. The recovery levels obtainable by the processes described herein are typically at least 50%, preferably 65%, and most preferably 80%, based upon the total of all forms of the particular isoflavone in the starting vegetable protein material. Although not wishing to be bound to any particular theory, it is believed that the high recoveries stem from the conversion reactions described herein coupled with the various processing operations also described. By converting glucone isoflavone conjugates, which are relatively soluble, to less soluble aglucone forms, at a particular stage of processing, it is possible to recover in the resulting product, a high percentage of the isoflavones from the feed material.

The following examples describe specific but non-limiting embodiments of the present invention.

Experimental

Samples were prepared by adding 5 grams of extracted, defatted soy flakes (flour) to 5 grams of water and the pH adjusted to 7 and to 8. 0.25 grams Lactase F or Lactozyme was added to each of the suspensions such that enzyme concentration was at about 5% by weight of the solids in each sample. Samples were incubated at 40° C. and at 60° C. A subsample was withdrawn before enzyme was added (t=0) and after 24 hours incubation at the target temperature. The change and percent distribution of isoflavones in soy flakes (flour) after the 24 hour incubation period with either Lactase P or Lactozyme is shown in Table 1. The samples were not sterilized before adding supplemental enzyme and microbial and contaminant growth was not inhibited.

TABLE 1

| SAMPLE | GENI-STIN % | 6"-OHAL GENI-STIN % | 6"-OAC GENI-STIN % | GENI-STEIN % | DIAD-ZIN % | 6"-OHAL DIAD-ZIN % | 6"-OAC DIAD-ZIN % | DIAD-ZIN % | GLY-CITIN % | 6"-OHAL GLY-CITIN % | GLY-CITEIN % |
|---|---|---|---|---|---|---|---|---|---|---|---|
| t = 0 | 16 | 80 | 0 | 4 | 16 | 79 | 1 | 3 | 22 | 62 | 16 |
| pH 7.0, 40C, t = 24 | | | | | | | | | | | |
| no added enzyme | 4 | 48 | 0 | 48 | 3 | 51 | 0 | 46 | 0 | 42 | 58 |
| lactase F | 2 | 39 | 0 | 59 | 2 | 41 | 0 | 57 | 0 | 30 | 70 |
| lactozyme | 3 | 45 | 0 | 51 | 2 | 49 | 1 | 48 | 0 | 40 | 60 |
| pH 7.0, 60C, t = 24 | | | | | | | | | | | |
| no added enzyme | 5 | 22 | 0 | 73 | 7 | 33 | 0 | 60 | 4 | 21 | 75 |
| lactase F | 10 | 32 | 0 | 59 | 10 | 35 | 3 | 52 | 6 | 23 | 71 |
| lactozyme | 4 | 22 | 0 | 74 | 5 | 33 | 0 | 62 | 0 | 23 | 77 |
| pH 8.0, 40C, t = 24 | | | | | | | | | | | |
| no added enzyme | 4 | 49 | 0 | 47 | 3 | 50 | 2 | 45 | 0 | 43 | 57 |
| lactase F | 3 | 39 | 0 | 58 | 3 | 40 | 3 | 55 | 0 | 29 | 71 |
| lactozyme | 5 | 46 | 0 | 49 | 4 | 48 | 0 | 47 | 0 | 40 | 60 |
| pH 8.0, 60C, t = 24 | | | | | | | | | | | |
| no added enzyme | 2 | 14 | 0 | 84 | 3 | 26 | 3 | 70 | 0 | 15 | 85 |
| lactase F | 6 | 24 | 0 | 80 | 8 | 30 | 3 | 59 | 5 | 22 | 74 |
| lactozyme | 2 | 14 | 0 | 84 | 3 | 24 | 6 | 67 | 0 | 16 | 84 |

These data indicate the degree of conversion attainable by a combination of residual enzyme(s) and supplemental enzyme(s). Source of residual enzyme may be microbial growth or endogenous soy enzymes. Significant conversion of isoflavone conjugates to aglucones occurred in soy flakes (flour) incubated at a pH of 8, 60° C., and for 24 hours. The concentration of each type of isoflavone described herein is based upon the total of all forms of that isoflavone type.

Another set of samples were prepared by forming 16% aqueous suspensions of defatted soy flakes. The samples were pH adjusted to 4.5 and 7, and incubated at 45° C. for 24 hours. Subsamples were taken at 0 and 24 hours. All samples were analyzed for isoflavone content. Table 2 shows the change in percent distribution of calculated isoflavones in defatted flakes after incubation for 24 hours at pH 4.5 and 7, and at 45° C.

room temperature with an orbital shaker. After 2 hours, the remaining undissolved materials are removed by filtration through Whatman No. 42 filter paper. Five ml of the filtrate are diluted with 4 ml of water and 1 ml of methanol.

The extracted isoflavones are separated by HPLC (High Performance Liquid Chromatography) using a Beckman C18 reverse phase column. The isoflavones are injected on to the column and eluted with a solvent gradient starting with 88% methanol, 10% water, and 2% glacial acetic acid and ending with 98% methanol and 2% glacial acetic acid. At a flow rate of 0.4 ml/min, all the isoflavones—genistin, 6"-O-Acetylgenistin, 6"-O-Malonylgenistin, genistein,

TABLE 2

| | GENISTIN % | 6"-OMAL-GENISTIN % | 6"-OAC-GENISTIN % | GENISTEIN % | DAIDZIN % | 6"-OMAL-DAIDZIN % | 6"-OAC DAIDZIN % | DAIDZEIN % | GLYCITIN % | 6"-OMAL-GLYCITIN % | GLYCITEIN % |
|---|---|---|---|---|---|---|---|---|---|---|---|
| t = 0 Flakes | 49 | 46 | 0 | 4 | 49 | 44 | 3 | 3 | 44 | 33 | 22 |
| 45° C., pH 7.0 t = 24 Flakes | 3 | 28 | 0 | 69 | 2 | 35 | 5 | 59 | 0 | 28 | 73 |
| 45° C., pH 4.5, t = 24 Flakes | 19 | 42 | 0 | 39 | 17 | 48 | 4 | 31 | 14 | 37 | 49 |

These data indicate the degree of conversion attainable by residual enzyme(s) in the protein material. Significant conversion of isoflavone conjugates to aglucones occurred at a pH of 7 and temperature of 45° C. after 24 hours incubation.

In another series of experiments, the percent recovery of genistein and daidzein in a protein isolate derived from soybeans was investigated. The percent recovery was found by determining the amount of genistein (or daidzein) in the isolate, and expressing that amount as a percentage based upon the total amount of all forms of genistein (or daidzein) in the soybean starting material. 100 g of defatted soy flour was extracted with 1,000 g of water, which was adjusted to a pH of 9.7 by the addition of sodium hydroxide at a temperature of 32° C. This provided a weight ratio of water to flour of 10:1. The flour was separated from the extract and re-extracted with 600 g of aqueous extract having a pH of 9.7 and a temperature of 32° C. The second extraction step provided a weight ratio of water to flour of 6:1. The flour was separated by centrifugation, the first and second extracts combined, and the pH adjusted to 4.5 to form a slurry of soy whey and acid precipitated curd. The slurry was heated to 50° C., and 2% by dry weight of the curd of the enzyme Lactase F was added. The slurry was allowed to react for 16 hours at 50° C. to ensure complete conversion of the glucone isoflavones to the aglucone form. The acid precipitated curd was separated from the whey by centrifugation to form an aglucone enriched isolate. Further washing of the precipitated curd with water was avoided. The amount of genistein recovered in the isolate was 86% of the total of all forms of genistin and genistein in the starting soybean material (defatted soy flour). Similarly, the amount of daidzein recovered in the isolate was 75%.

The following is a description of a method for quantifying isoflavones in soy products. The isoflavones are extracted from soy products by mixing 0.75 gram of sample (spray dried or finely ground powder) with 50 ml of 80/20 methanol/water solvent. The mixture is shaken for 2 hours at daidzin, 6"-O-Acetyldaidzin, 6"-O-Malonyldaidzin, daidzin, glycitin and its derivatives and glycitein—are clearly resolved. Peak detection is by UV absorbance at 262 mm. Identification of the peaks is performed by mass spectrometer.

Quantification is achieved by using pure standards (genistin, genistein, daidzin and daidzein) purchased from Indofine Chemical Company, Sommerville, N.J. Response factors (Integrated area/concentration) are calculated for each of the above compounds and are used to quantitate unknown samples. For the conjugated forms for which no pure standards are available, response factors are assumed to be that of the parent molecule but corrected for molecule weight difference. The response factor for glycitin is assumed to be that for genistin corrected for molecular weight difference.

This method provides the quantities of each individual isoflavone. For convenience, total genistein, total daidzein and total glycitein can be calculated and represent the aggregate weight of these compounds if all the conjugated forms are converted to their respective unconjugated forms. These totals can also be measured directly by a method using acid hydrolysis to convert the conjugated forms.

Of course, it is understood that the foregoing are merely preferred embodiments of the invention and that various changes and alterations can be made without departing from the spirit and broader aspects thereof as set forth in the appended claims, which are to be interpreted in accordance with the principals of patent law including the Doctrine of Equivalents.

What is claimed is:

1. A vegetable protein isolate comprising a protein isolate having a dry basis genistein content of about 1.5 mg/g to about 3.5 mg/g.

2. A vegetable protein isolate comprising a protein isolate having a dry basis daidzein content of about 1.0 mg/g to about 3.0 mg/g.

* * * * *